(12) United States Patent
Xu et al.

(10) Patent No.: US 8,338,151 B2
(45) Date of Patent: Dec. 25, 2012

(54) METHOD FOR CREATING INTRACELLULAR ARTIFICIAL NANOSTRUCTURES IN SITU

(75) Inventors: Bing Xu, Newton, MA (US); Zhimou Yang, Mountain View, CA (US); Keming Xu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 974 days.

(21) Appl. No.: 12/194,554

(22) Filed: Aug. 20, 2008

(65) Prior Publication Data
US 2010/0093084 A1    Apr. 15, 2010

Related U.S. Application Data

(63) Continuation-in-part of application No. 12/063,079, filed as application No. PCT/US2006/008333 on Mar. 6, 2006, now abandoned.

(60) Provisional application No. 60/706,072, filed on Aug. 8, 2005.

(51) Int. Cl.
*C12N 1/04* (2006.01)
*C12N 9/00* (2006.01)

(52) U.S. Cl. ........ 435/183; 435/325; 435/243; 424/488; 424/484

(58) Field of Classification Search ............... 435/325, 435/4, 183, 243; 424/488, 484
See application file for complete search history.

(56) References Cited

U.S. PATENT DOCUMENTS
2007/0224273 A1 *  9/2007  Xu et al. ................. 424/488

* cited by examiner

*Primary Examiner* — Ruth Davis
(74) *Attorney, Agent, or Firm* — Saliwanchik, Lloyd & Eisenschenk

(57) ABSTRACT

A method of creating intracellular artificial nanostructures in situ, which employees a chemical precursor. The precursor does not self-assemble due to the presence of a cleavable motif linked to it. When the precursor comes inside live cells by an uptaking mechanism on the cell membrane, the cleavable motif is then to be removed by an enzymatic action of a first enzyme. Without the cleavable motif, the precursor now engages in a self-assembling process to form nanostructures within the live cells, which may cause formation of a hydrogel. Furthermore, the self-assembling process can be made reversible by employing a second enzyme which puts the cleavable motif back to the precursor, whereby dissolving the nanostructures into solution.

16 Claims, 11 Drawing Sheets

Precursor compound (Ia)

Precursor compound (IIa)

FIG. 11

| Plasmid | E. coli IPTG | Overexpression of phosphatase | IC$_{50}$ (μg mL$^{-1}$) | | | |
|---|---|---|---|---|---|---|
| | | | IIa Nap-FFY(p) | IVa Nap-DFDFY(p) | Va Nap-β$^3$-HPhg-β$^3$-HPhgY(p) | |
| + | + | yes | 20 | 20 | 20 | |
| + | − | no | >2000 | >2000 | >2000 | |
| − | + | no | >2000 | >2000 | >2000 | |

METHOD FOR CREATING INTRACELLULAR ARTIFICIAL NANOSTRUCTURES IN SITU

CROSS REFERENCE TO RELATED APPLICATIONS

This is a continuation-in-part application of U.S. application Ser. No. 12/063,079, filed Feb. 6, 2008, now abandoned which is a national phase of PCT Application No. PCT/US2006/008333, filed Mar. 6, 2006, which claims benefit of U.S. Provisional Application No. 60/706,072, filed Aug. 8, 2005, the contents of which are incorporated herein in its entirely by reference.

FILED OF THE INVENTION

This invention relates to formation of intracellular artificial nanostructures. Particularly, it relates to in situ formation of intracellular nanostructures initiated by an enzymatic action on non-native, man-made precursor compounds.

BACKGROUND OF THE INVENTION

Self-assembly, a fundamental process at all scales, plays a vital rule in biology and provides an important guidance for design and fabrication of functional materials. Particularly, self-assembly provides an attractive and practical methodology for creating artificial nanostructures that promise broad impacts and applications in the emerging field of nanoscience: for examples, self-assembled nanoparticles may lead to novel optical materials and high density magnetic recording media; the self-assembled monolayers have enabled nanometer thickness organic films to be constructed on a variety of substrates for modeling biological surface to control the fate of cells, building molecular electronic devices, developing nanolithography, and generating nanostructures for biomedical diagnostics. The self-assembly of oligopeptides and other organic molecules has resulted in nanofibers as the functional matrices of hydrogels that are useful for tissue engineering, inhibitor screening, and wound healing. Although these works reflect exciting and important development of self-assembled nanostructures in extracellular settings or a non-biological arena, intracellular creation of artificial nanostructures remains unexplored and its subsequent biological effects unknown despite of its significances and potential applications.

Exploring intracellular artificial nanostructures is significant for several reasons. First, self-assembled nanostructures such as cell membranes, strands of nucleic acids, and actin filaments, prevail in living cells and are indispensable for critical cellular functions (i.e., as structural motifs for maintaining integrity of cells, as effective storages for keeping genetic information, and as active devices for regulating numerous of cellular processes), therefore intracellular artificial nanostructures provide an attractive and effective strategy from perturbing the cellular activities to managing the behaviors of cells. Second, many diseases are related to mishaps in cellular nanostructures (i. e., mismatch of base pairs, formation of β-amyloid, and misfolding of proteins), and hence intracellular artificial nanostructures offers a versatile platform for mimicking, modeling, and understanding the mechanism of diseases, thereby developing the therapeutic approaches. Third, great advances in molecular cell biology, such as the study of biological process at the molecular level, during the last five decades have led to new insights into the evolution of life form, and now there is a need to correlate biological process beyond molecule level and to understand structure and dynamics as a system (i.e., system biology). Self-assembled intracellular artificial structures at nanoscale would lend a convenient means to examine the structure and dynamics of cellular and organismal function and to allow previously unconnected domains of knowledge to be understood at new levels of complexity.

Because nanostructures created in situ within live cells have wide potential applications as discussed in the above, there is a need for a convenient method to create intracellular artificial nanostructures.

SUMMARY OF THE INVENTION

An object of the present invention is to provide a method of enzyme-triggered creation of intracellular nanostructures from human-designed chemical precursors. The method comprises the steps of (a) designing a chemical precursor having a cleavable motif by an enzyme, (b) introducing the precursor into the cells, and (c) removing the cleavable motif from the precursor by an enzyme, thereby making the precursor self-assemble into nanostructures inside the cell.

Another object of the present invention is to provide a method of enzyme-controlled switch between the gelation and solution states of the intracellular artificial nanostructure. This is achieved in the present invention through designing a precursor that is susceptible to a pair of enzymes: one enzyme capable of removing the cleavable motif from the precursor and the other enzyme capable of putting it back on. This enzyme pair can control the sol-gel phase transition of the nanostructure formed inside the cells, serving as a useful research model or tool.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

BRIEF DESCRIPTION OF DRAWINGS

FIG. 11 presents the $IC_{50}$ values of different precursors (IIa, IVa and Va) of hydrogelators against E. coli with/without overexpression of phosphatase (expression of phosphatase controlled by the addition of plasmids and IPTG, Y(p)=tyrosine phosphate).

DETAILED DESCRIPTION OF PARTICULAR EMBODIMENTS OF THE INVENTION

A. Precursor

Precursors suitable for practicing the present invention can be designed according to the guide provided in the following.

The basic structure of the precursor for enzymatic hydrogelation should contain three groups or motifs: (1) a hydrophobic group; (2) a hydrophilic group; and (3) a cleavable group.

A proper precursor suitable for practicing the present invention should not self-assemble before entering the cell and should be synthesized consisting of three distinct motifs/groups: (1) the hydrophobic group, such as, for example, a napthyl ($C_{10}H_7CH_2-$), linear or branched alkyl (CnH2n+1, n=4-30), or aromatic group, for providing the hydrophobic force to enhance self-assembly in an aqueous environment; (2) the molecular or nanoscale segment (such as, for example, single amino acid residue, dipeptide, phe-phe or X-Y, where X and Y are amino acid residues, and tripeptide, tetrapeptide, pentapeptide, aminoglycoside, fluoroquinolone, bisphosphonate, antibiotic, antineoplastic, antifungal, antiparasitic molecule, iron oxide nanoparticle (5 to 50 nm), etc.) being the major building blocks for self-assembly besides acting as hydrogen bonds acceptors and donors to interact with water; and (3) the cleavable group (such as, for example, butyric dicarboxylate acid, bisphosphonates, phosphates, carbohydrates, etc.), which covalently links to the segment by a link for tailoring the overall balance of the hydrophobic and hydrophilic interactions so that the precursor would not self-assemble into a nanostructure, which are designed to happen only upon removing the cleavable group by an enzymatic action. With the foregoing guideline, people with ordinary skill in the art are able to design various precursors tailored to their particular needs for creating nanostructure in situ within the cell. It is understood that the forgoing specific components listed for each motif/group are by way of example only, not limitation to the present invention.

Figure 1:
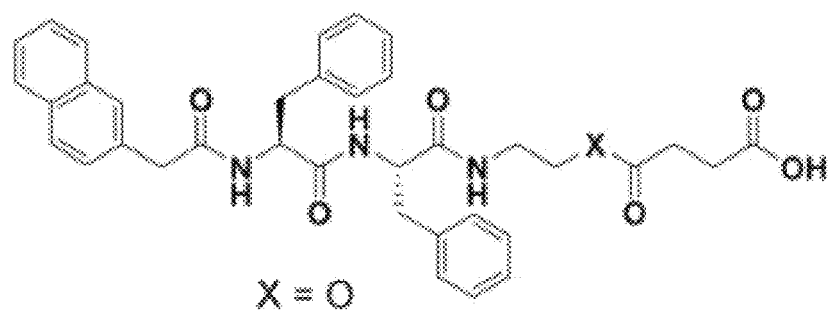
FIG. 1 shows the chemical structure of two precursor compounds Ia and IIa according to the present invention.
Figure 1:
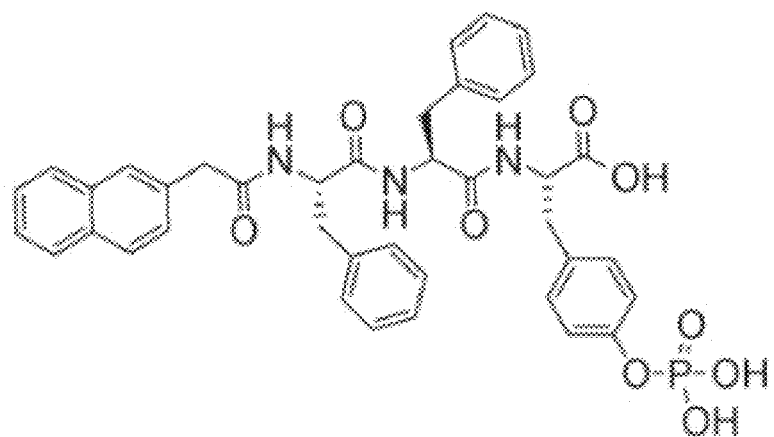

The following precursor compounds have been designed as particular examples, which are shown in FIG. 1 as precursor compounds (Ia) and (IIa), respectively. Following the aforementioned guideline, each of the precursors has three motifs: a napthyl group, the molecular or nanoscale segment, and a cleavable group. In general, an in vitro experiment can be conducted to quickly confirm whether a particular design of precursor suitable for practicing the present invention, i.e., a precursor for forming intracellular nanostructures in situ, as exemplified in the following.

Figure 2A:
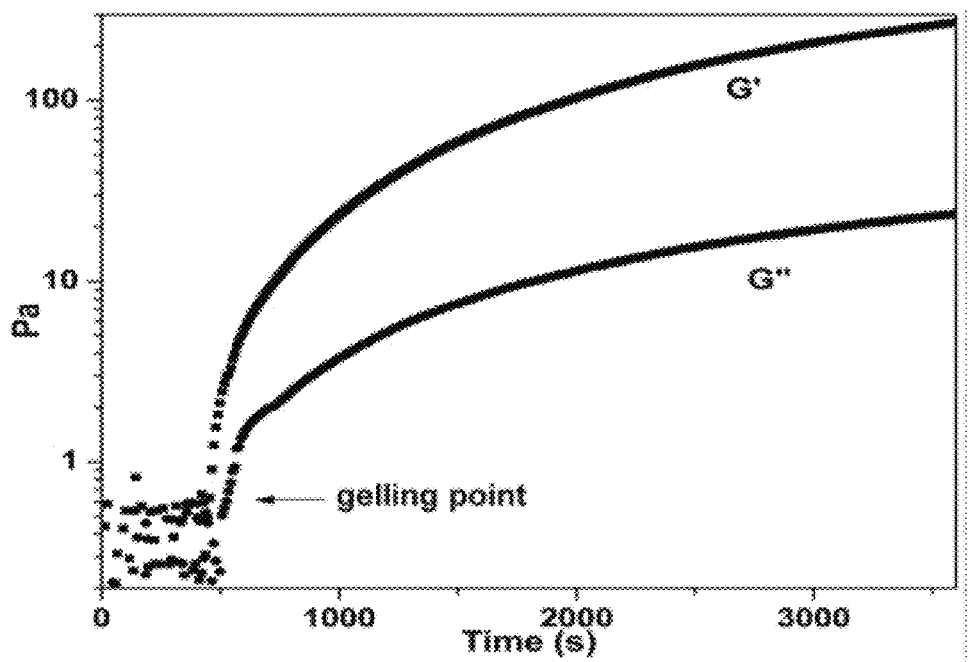
FIG. 2A is oscillatory rheology of a solution containing 8 mM (0.5 wt %) of Ia and 0.2 mg of enzyme solution, pH=8.0, 37° C.
Figure 2B:
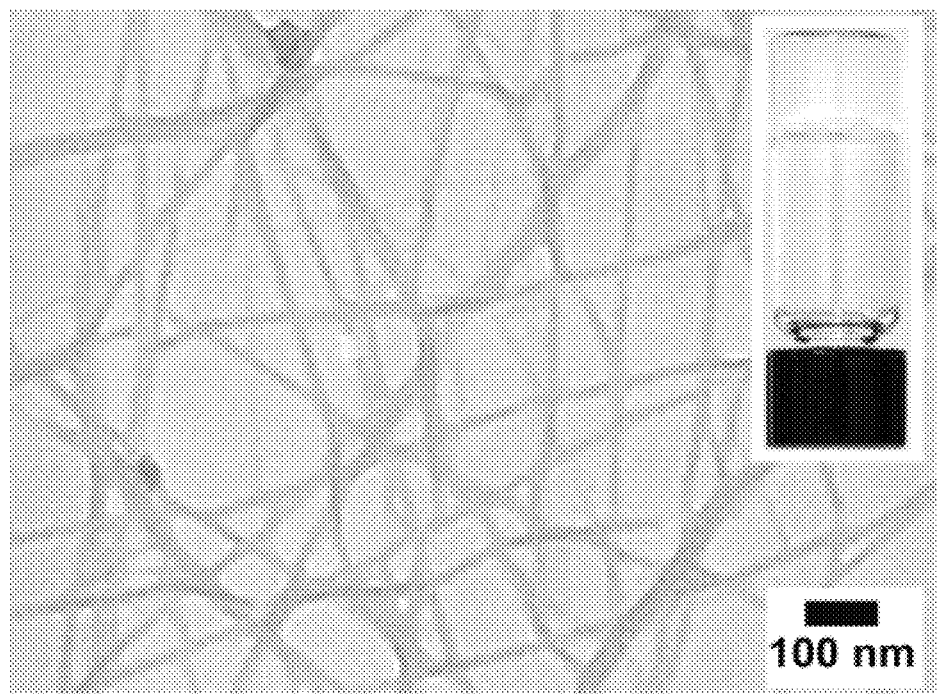
FIG. 2B is a TEM image of the hydrogels (inset: optical image) formed by Ia via enzymatic gelation in water (concentration=0.5 wt %, pH=8.0).

In an in vitro experiment to characterize the properties of precursor Ia, the fact that an esterase can convert Ia to IA, lead to the formation of nanofibers, and induce hydrogelation was verified. At pH about 8.0, adding 0.1 mL of the esterase (7 U of esterase in 1 mL of distilled water with pH adjusted to 8.0) to 0.9 mL solution of Ia (0.5 mg) and keeping the solution at 37° C. for about 6 minutes resulted in formation of the hydrogel, which is stable even upon heating to near 100° C. Rheological experiments (shown in FIG. 2A) reveal that the hydrogel started to form in less than 10 minutes, as indicated by the storage modulus (G') dominating the loss modulus (G"). This enzyme-catalyzed hydrogelation completes in 100 minutes, as indicated by the (G') storage modulus reaching plateau. $^1$H NMR suggests 68% of Ia transforms to IA (that is Ia with the cleavable motif removed) at this stage. The formed hydrogel of IA is transparent (inset, FIG. 2B) suggesting that there is no microcrystalline aggregate in the hydrogel to scattering visible light, which agrees with the transmission electron micrograph (TEM) of the hydrogel (FIG. 2B). In addition, TEM shows that the size of the nanofibers formed by the self-assembly of IA is about 10 nm, though the bundles of the nanofibers reach the size as wide as about 60 nm.

Figure 4:
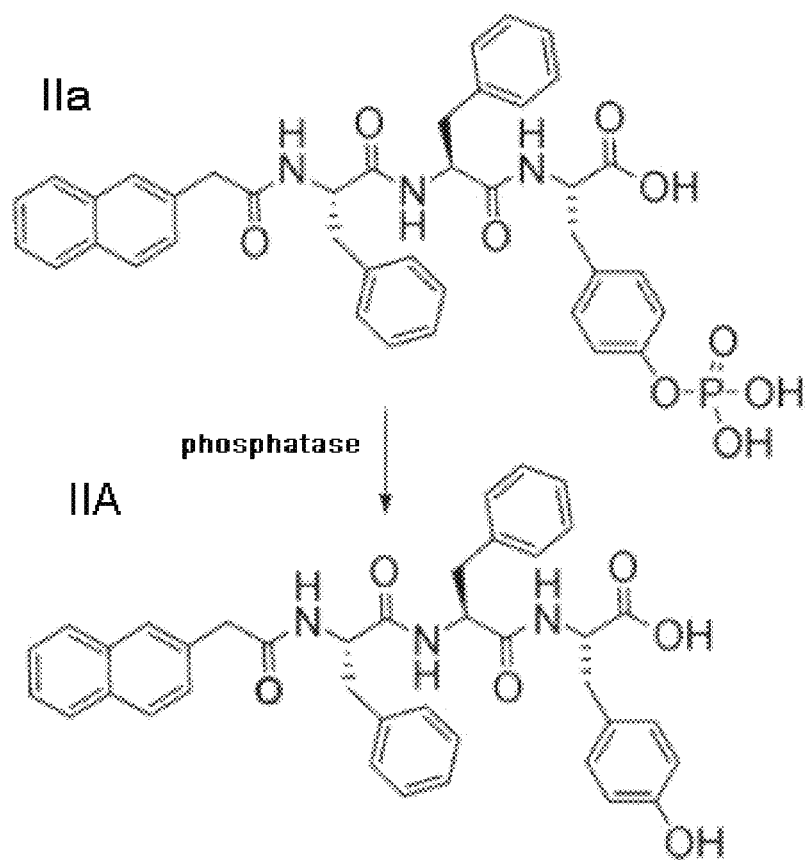
FIG. 4 shows the enzymatic action by a phostaphase on precursor IIa of the present invention.

Similar results were obtained with respect to precursor compound (IIa). In this embodiment, precursors bearing the general formula $C_{10}H_7CH_2C(O)-ZZ$ (where Z is the residue of an amino acid) was used. Amount them, the precursor compound $C_{10}H_7CH_2C(O)$-L-Phe-L-Phe exhibited the lowest minimum gelation concentration (mgc; ca. 0.4%). This result is consistent with the observation of Gazit and coworkers that the Phe-Phe motif is prone to self-assembly in water. To be accessible to an enzyme, the molecule is phosphorylated at its C terminal with tyrosine phosphate to afford $C_{10}H_7CH_2C(O)$-L-Phe-L-Phe-Tyr-$(PO(OH)_2)$, referred to as IIa. As shown in FIG. 4, a tyrosine phosphatase cleaves the phosphate residue from IIa and generates the more hydrophobic $C_{10}H_7CH_2C(O)$-L-Phe-L-Phe-Tyr (IIA), which then self-assembles into nanofibers to form a hydrogel.

Figure 5A:
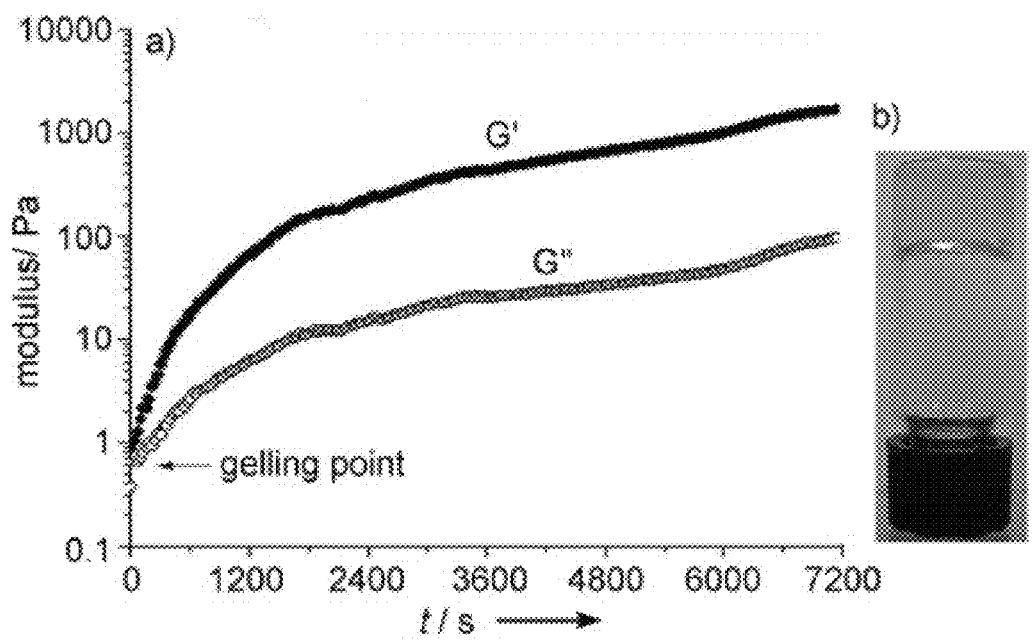
FIG. 5A is (a) oscillatory rheology of a PBS buffer solution containing 6.91 mm (0.5 wt %, 5000 ug mL$^{-1}$) of IIa and 10 uL of enzyme solution, pH 7.4, 25° C. and (b) optical image of the hydrogel.
Figure 5B:
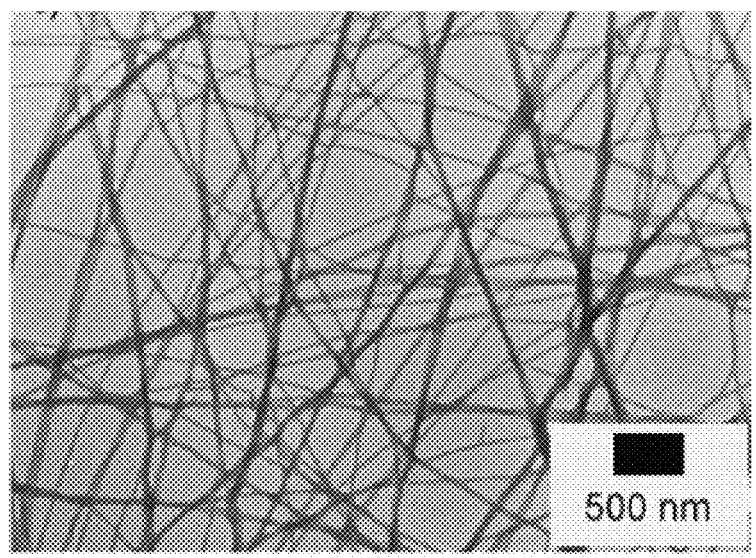
FIG. 5B is a TEM image of the hydrogels formed by IIa via enzymatic gelation in a PBS buffer solution (concentration=0.5 wt %).

As shown in FIG. 5, it was demonstrated that an alkaline phosphatase could convert IIa into IIA, lead to the formation of nanofibers, and induce hydrogelation in vitro. Adding alkaline phosphatase (700 U $mL^{-1}$) to a phosphate saline buffer (PBS) solution of IIa (0.5 wt %, 6.91 mM) resulted in a hydrogel. Rheological tests (FIG. 5A, a) revealed that the hydrogel started to form almost instantly after the phosphatase was added at room temperature, as indicated by the storage modulus (G') dominating the loss modulus (G"). According to HPLC analysis, about 48% of IIa transformed into IIA at the gelling point. The transparency of hydrogel IIA (FIG. 5A, b) suggests that no microcrystalline aggregates formed in the hydrogel to scatter visible light. A transmission electron micrograph (TEM) of the hydrogel (FIG. 5B) showed that the diameter of the nanofibers formed by the self-assembly of IIA was about 26 nm. The experiment also showed that the mgc of IIA was between 0.025 and 0.05 wt % in the PBS solution.

Figure 6:
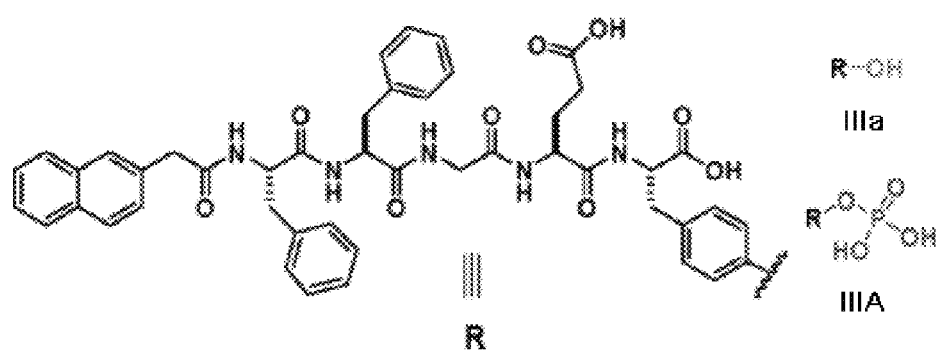
FIG. 6 shows the chemical structure of a precursor IIIa/IIIA that can be subject to an enzymatic switch according to the present invention.

As another example of designing precursor for practicing the present invention, Nap-FFGEY referred to as precursor IIIa here (shown in FIG. 6) was made. This precursor was designed so that an intracellular nanostructure is formed which can switch between a gelation state and a solution state subject to relative concentrations of kinase and phosphatase. The design considerations and in vitro testing are described in the following.

For this precursor, it is possible to use the enzyme kinase/phosphatase pair as an enzyme switch because (i) FF is prone to self-assembly (ii) Nap-FF gels water effectively (at 0.8 wt %), and (iii) the residue of Glu-Tyr (EY) accepts phosphorylation in the presence of a tyrosine kinase and the phosphorylation process can be reversed by phosphatase.

One of the motivations to use naphthalene (Nap) rather than N-(fluorenyl-methoxycarbonyl) (FMOC) is that Nap should be more biocompatible, as evidenced by several clinical drugs consisting of a Nap motif (i. e., propranolol, naphazoline, nafronyl). The glycine (G) was used to connect Nap-FF with EY because glycine is the simplest amino acid. Unlike other pentapeptides, FFGEY is not a known epitope of any protein, but it carries the basic structural requirement to serve as the substrate of the tyrosine kinase. After obtaining precursor IIIa through solid-phase synthesis, the hydrogelation ability of IIIa was tested. Via a slight adjustment of pH (from 7.8 to 7.5), IIIa forms a transparent hydrogel in water at 0.6 wt %). The successful hydrogelation of IIIa implies that Nap-FF also may act as a useful motif to conjugate with other amino acid residues to construct hydrogelators.

Figure 7:
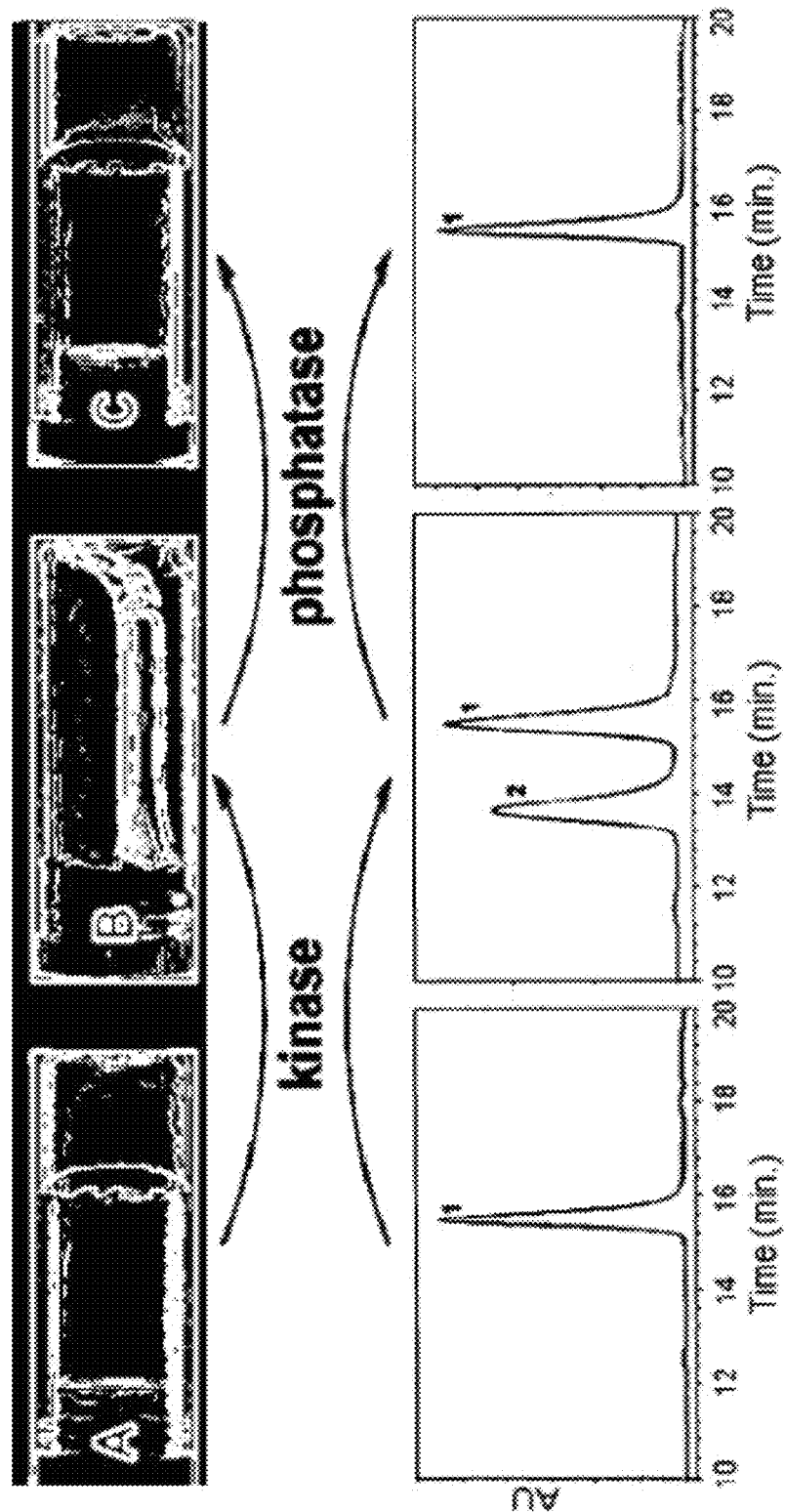
FIG. 7 is optical images and corresponding HPLC traces of (A) gel I; (B) the solution obtained after adding a kinase to gel I; and (C) gel II.

After confirming that IIIa is indeed an efficient hydrogelator, the use of the kinase/phosphatase switch to control the phase transition of the hydrogel was examined. The addition of 1 (3 mg) into a buffer (0.5 mL, containing 10 mM of ATP) creates a transparent hydrogel (gel I, FIG. 7, A) in 5 min. Then, 3 U of tyrosine kinase (50 µL) was added on the top of gel I to initiate phosphorylation of IIIa. After 24 h, gel I turned into a clear solution (FIG. 7, B). An HPLC test of the solution confirmed that about 46% of IIIa was converted to IIIA. Because the phosphate groups of IIIA repel each other to weaken the self-assembly of the nanofiber and render IIIA more hydrophilic than Ina, the gel-sol phase transition occurs. The addition of about 200 U of alkali phosphatase (10 µL) into the solution restores the hydrogel (gel II, FIG. 7, C) in 1 h. After another 4 h, HPLC analysis showed that 99.1% of IIIA transformed back to IIIa. Because the catalytic activity of the phosphatase used in this experiment is about 1000 times higher than that of kinase, one cycle of the gel-sol-gel transformation was able to be completed. To cycle such a transformation many times, one might need to adjust the relative amounts of a pair of enzymes that have similar activities. Nevertheless, the result demonstrated here validates the concept of the regulation supramolecular hydrogels by an enzyme switch. In addition, the new insight of the dynamic cell signaling suggests that a stimulus tips the protein kinase (PK)/protein phosphatase (PP) balance by simultaneously activating PKs and deactivating PPs. This model implies that it would be easier to cycle the phase transition of the supramolecular hydrogel in vivo using proper hydrogelators as the substrates, which may, for example, lead to a drug delivery system that responds to biological activities of tissues.

B. In Situ Creation of Nanostructure within Cells

Figure 8:
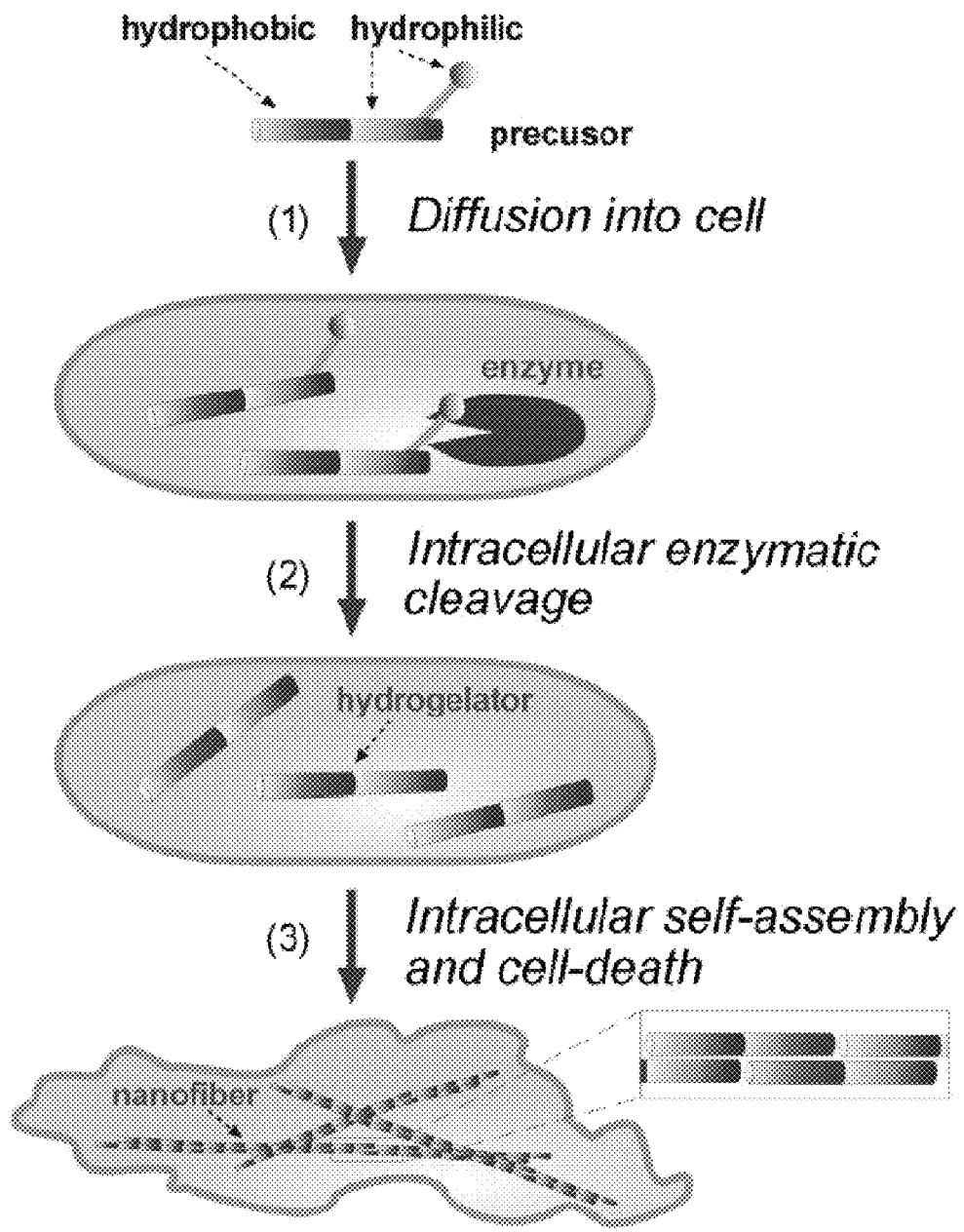
FIG. 8 is a schematic representation showing the steps involved in the process of forming intracellular artificial nanostructures in situ according to the present invention.

With reference to FIG. 8, which outlines the steps involved in creating nanostructures in situ within the live cell. A precursor, which does not self-assemble before coming inside the cell, enters the cell by, but not limited to, a simple diffusion process or other process known and commonly used in the art, such as any active transporting mechanism present on the cell membrane. Once the precursor is inside the cell, an enzyme expressed in the cell converts the precursor into a hydrogelator that can self-assembled into nanofibers, which is one of simple nanostructures. The formation of nanofibers can lead to hydrogelation, which exerts stresses on the cell, and cause cell death, an easily observable cellular transition.

Nanostructure Formation In Situ within Hela Cells Using Esterase

Figure 3:
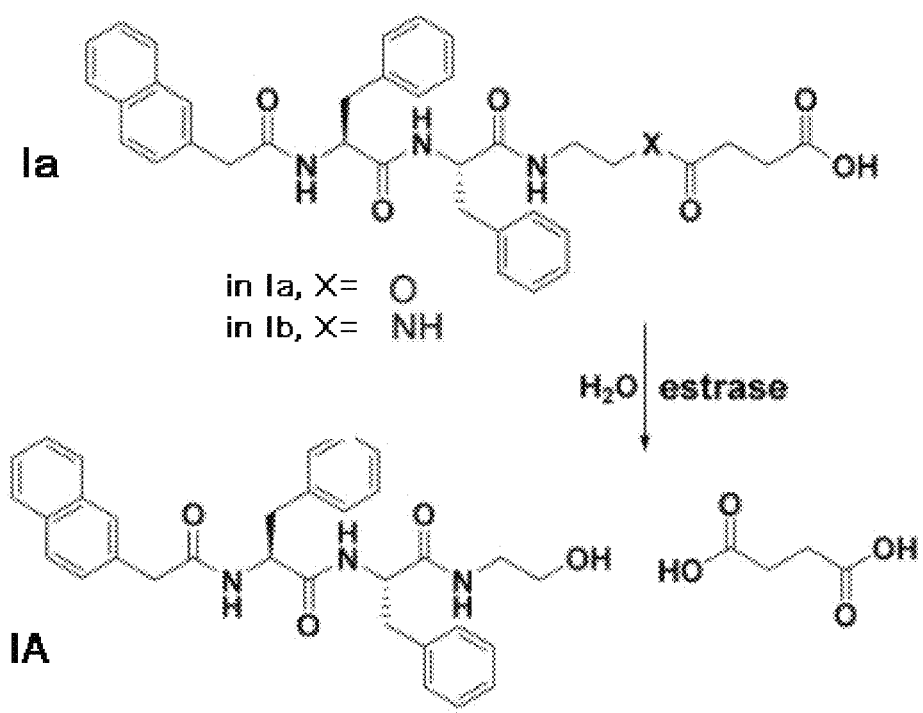
FIG. 3 shows the enzymatic action by an esterase on precursor Ia of the present invention.
Figure 9:
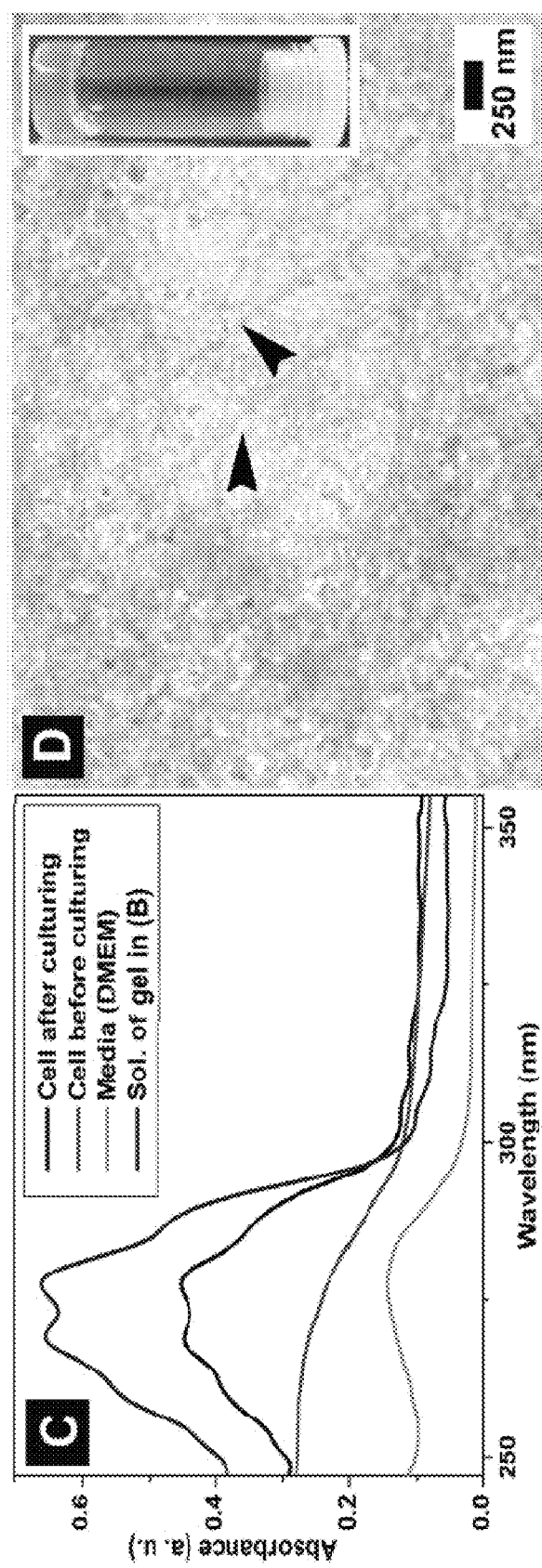
FIG. 9 shows (C) the UV spectra of the solution of the gel in FIG. 2B, of the cell culture media (DMEM), and of the HeLa cells before and after culturing with Ia; and (D) TEM of the hydrogels formed by the dead HeLa cells after culturing with Ia for three days (arrows indicates the nanofibers formed by IA and inset is optical image of the hydrogel).

Referring to FIG. 3, compound Ia is a precursor whose cleavable motif can be removed by esterase. As demonstrated in the above, esterase could covert Ia into IA in vitro. In the following, the same conversion is shown to occur within Hela cells once Ia is uptaken by the cell. Hela cells were incubated in the presence of compound Ia (initially at a concentration of 0.08%), the characteristic absorption peaks of the naphthyl group in the culture solution and the Hela cells were monitored to estimate the amount of the precursor uptaken by the cells. After culturing with Hela cells had proceeded for three days, the absorption of the naphthyl group dropped 32% in the culture solution. Concurrently, the absorption of the naphthyl appeared on the Hela cells. Furthermore, the shape and position of the absorption peak is identical to the absorption spectra of the hydrogel formed by conversion of Ia to IA using esterase in vitro shown in the forgoing, suggesting that intracellular hydrogelation had occurred. It is expected as the volume of the cells is less than 1% of the volume of the culture media and the concentration of Ia inside the cells easily reaches above the mgc of IA. Once these molecules of Ia are converted to IA by endogenous esterases, it should self-assemble into nanofibers. To confirm this, the dead Hela cells that were detached from the surface of the culture solution were collected. After using centrifuge to remove the extracellular water, the cells were broken and observed the formation of hydrogel (inset, FIG. 9, D). Transmission electro microscopy TEM (FIG. 9, D) reveals that the formation of nanofibers with the width of 25 nm and morphology similar to the nanofibers formed by the IA alone. Live Hela cells were collected that adhered to the surface of petri dish. After being broken by ultrasound, the cell debris neither forms hydrogel nor shows long nanofibers under TEM. These results confirm that the cell death is associated with intracellular formation of the nanofibers and the hydrogelation.

Nanostructure Formation In Situ within E. Coli Cells Using Phosphatase

To demonstrate intracellular enzymatic hydrogelation of precursor compound IIa, isopropyl-b-d-thiogalactopyranoside (IPTG) and plasmids were used to induce the overexpression of phosphatase in an E. coli strain according to a commonly used literature protocol. After confirming the successful overexpression of phosphatase within the E. coli (BL21) using sodium dodecyl sulfate polyacrylamide gel electrophoresis (SDS-PAGE, FIG. 10, a), Ia (75 µg mL$^{-1}$, 10.4 µM) was added to the culture medium. After incubation for 24 h at 18° C., the bacteria were harvested, washed three times with PBS buffer, and lysed in dimethyl sulfoxide to dissolve the organic compounds from the cells for HPLC analysis.

Figure 10:
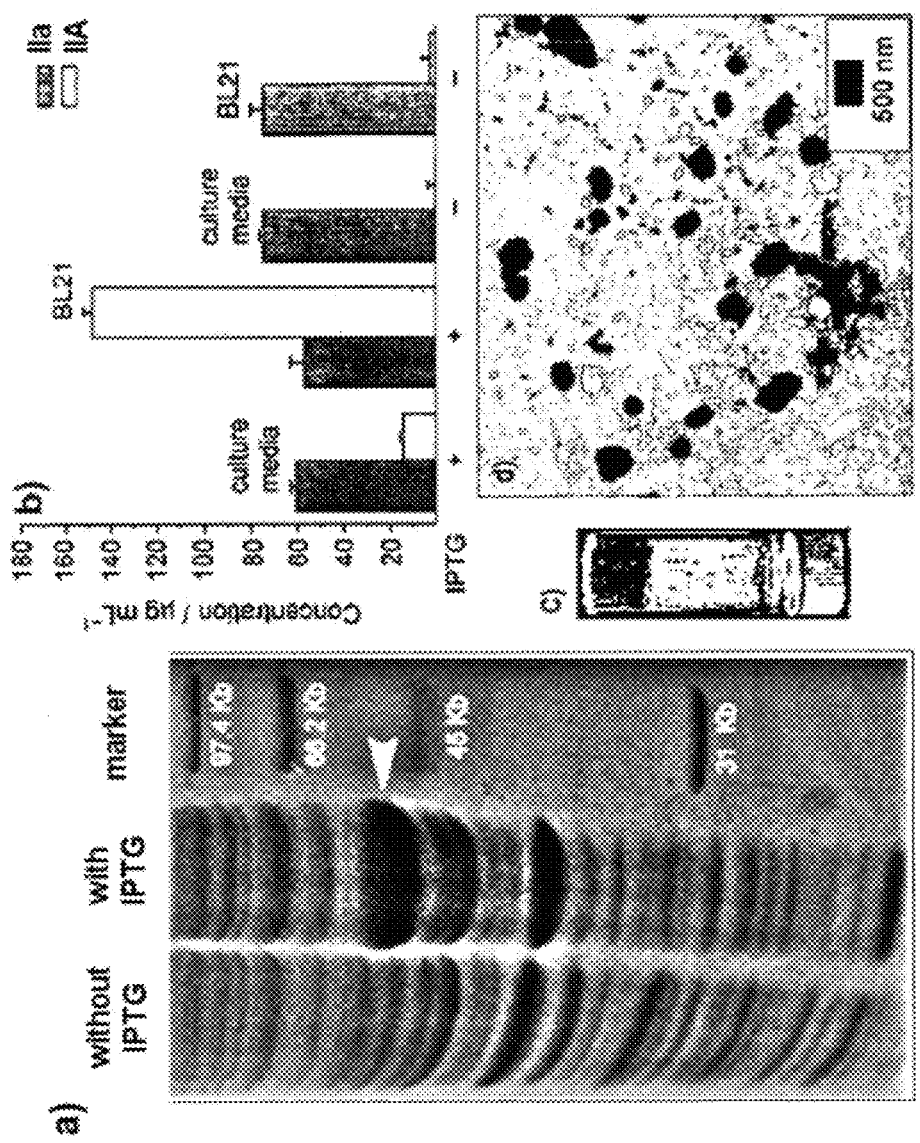
FIG. 10 shows (a) SDS-PAGE distribution of cell lysates of E. coli BL21 (the phosphatase is indicated by the arrow); (b) concentrations of IIa and IIA in the culture medium and within the cells (BL21, plasmid+, IPTG+ or IPTG−); (c) optical image of the hydrogel; and (d) TEM images of the hydrogel formed inside the bacteria after culturing with IIa for 24 h (arrows indicate the nanofibers formed by IIA).

The results indicated significant conversion of IIa into IIA within the bacteria: The total concentration of IIa plus IIA was 230 µg mL$^{-1}$ within the bacteria (BL21, plasmid+, IPTG+) and 75 µg mL$^{-1}$ in the culture medium (FIG. 10, b). The intracellular concentration of IIA (=148 µg mL$^{-1}$) was significantly higher than that in the culture medium (=15 µg mL$^{-1}$), confirming not only the successful enzymatic conversion of IIa into IIA, but also its accumulation inside the bacteria. The concentration of IIA inside the cells also agreed with the fact that IIA is more hydrophobic than IIa. Once formed inside a cell by the enzymatic reaction, IIA tended to stay and self-assemble inside the cell. Though lower than the mgc of IIA (500 µg mL$^{-1}$) required to gel the PBS buffer solution, the concentration of IIA inside the E. coli (148 µg mL$^{-1}$) is higher than the mgc (125 µg mL$^{-1}$) needed for gelling the bacterium's cytoplasm, as determined in a control experiment. This result indicates that hydrogelation was able to proceed intracellularly.

To further prove that hydrogelation occurred within the cells, bacteria were incubated with IIa, collected, and lysed by using ultrasound. The resulting suspension formed a supramolecular hydrogel (FIG. 10, c) whose TEM image also confirmed the presence of nanofibers (FIG. 10, d). There was no phosphatase overexpression observed when BL21 with plasmids was treated with compound IIa without IPTG. Furthermore, the absence of IIa resulted in neither a hydrogel nor nanofiber formation (data not shown). Because Congo red can selectively stain the hydrogel of IIA, it was used to stain the E. coli after they had been incubated with IIa for 24 h. The Congo red could only stain E. coli with overexpressed phosphatase and incubation with IIa, indicating the formation of a hydrogel of IIA. These results demonstrate that the overexpression of phosphatase dictates the formation of nanofibers and of a hydrogel of IIA within the bacteria.

Additionally, IIa was tested at various concentrations to examine the effective concentration required for bacteria inhibition. As shown in FIG. 11, IIa exhibited an IC$_{50}$ value of 2.77 µM (20 µg mL$^{-1}$) against the bacteria that overexpressed phosphatase. This value was more than 100-fold lower than the IC$_{50}$ value of II a (greater than 2000 µg mL$^{-1}$, 277 µM) against the bacteria without the overexpression of phosphatase. In a control experiment, IIa showed no inhibition effects (IC$_{50}$>2000 µg mL$^{-1}$, 277 µM) on the bacteria (BL21 with plasmid or without plasmid) in the absence of IPTG, thus confirming that the up-regulation of the enzymes is critical for the formation of hydrogelators and the inhibition of bacterial growth. In addition, HPLC analysis showed that the concentrations of IIa (75 µg mL$^{-1}$) and IIA (3 µg mL$^{-1}$) inside the E. coli (BL21, plasmid+, IPTG−) without the overexpression of phosphatase were almost same as those in the culture medium ([IIa]=75 µg mL$^{-1}$ and [IIA]=1 µg mL$^{-1}$), suggesting that the phosphatase-catalyzed accumulation of IIA within the bacteria was critical for the inhibition. Moreover, the structural variants of IIa, precursors IVa and Va, which formed hydrogels upon the addition of the phosphatase, exhibited inhibitory effects (FIG. 11, IC$_{50}$<2.77 µM) similar to that of IIa against the E. coli that overexpressed phosphatase. Because of their different stereo- and region-chemical structures, the inhibitory properties of IIa, IVa, and Va could not be ascribed to a specific ligand-receptor interaction. The results confirm that the formation of supramolecular nanofibers and hydrogelation within the bacteria inhibit bacterial growth.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

We claim:

1. A method of creating a nanostructure in a live cell, comprising the steps of:
   (a) preparing a chemical precursor comprising a cleavable motif;
   (b) introducing said precursor into a live cell; and
   (c) after said precursor is introduced into said live cell, removing said cleavable motif from said precursor with an enzyme to allow said precursor to self-assemble into a nanostructure inside said live cell.

2. The method of claim 1, wherein said chemical precursor further comprises a hydrophobic motif and a hydrophilic motif.

3. The method of claim 2, wherein said hydrophobic motif is a napthyl, aromatic, or alkyl group, said alkyl group being linear or branched, of a formula $C_nH_{2n+1}$, where n is 4-30.

4. The method of claim 2, wherein said hydrophilic motif is a water-soluble peptide, carboxylate aminoglycoside, or water-soluble therapeutic agent.

5. The method of claim 4, wherein said water-soluble peptide comprises 2-5 amino acid residues.

6. The method of claim 4, wherein said therapeutic agent is an antibiotic, antineoplastic, antifungal, antiparasitic molecules, or iron oxide nanoparticles.

7. The method of claim 1, wherein said cleavable motif is a phosphate, bisphosphonate, butyric acid, butyric dicarboxylate acid, carbohydrate, sulfate, ammonium, or ethylene glycol.

8. The method of claim 1, wherein said enzyme is esterase or phosphatase.

9. The method of claim 8, wherein said enzyme is expressed from a plasmid comprising a gene encoding said enzyme.

10. The method of claim 1, wherein said live cell is a mammalian cell.

11. The method of claim 1, wherein said live cell is a bacterium cell.

12. The method of claim 1, wherein said precursor is introduced into said live cell by a passive diffusion process.

13. The method of claim 1, wherein said precursor is introduced into said live cell by an active membrane transferring mechanism present in said live cell.

14. The method of claim 1, comprising a further step (d): dissolving said nanostructure into a non-assembled state by using another enzyme to link said cleavable motif back to said precursor.

15. The method of claim 14, wherein said enzyme and said another enzyme form an enzymatic switch that controls the sol-gel balance of said nanostructure.

16. The method of claim 15, wherein said enzyme is esterase and said another enzyme is phosphatase.

* * * * *

UNITED STATES PATENT AND TRADEMARK OFFICE
CERTIFICATE OF CORRECTION

PATENT NO. : 8,338,151 B2
APPLICATION NO. : 12/194554
DATED : December 25, 2012
INVENTOR(S) : Bing Xu, Zhimou Yang and Keming Xu Page 1 of 2

It is certified that error appears in the above-identified patent and that said Letters Patent is hereby corrected as shown below:

In the Specification

Column 1,
Lines 13-14, "in its entirely" should read --in its entirety--.
Line 16, "Filed" should read --Field--.
Lines 25-26, "a vital rule" should read --a vital role--.
Line 31, "for examples" should read --for example--.
Line 35, "surface" should read --surfaces--.
Line 46, "despite of its significances" should read --despite its significance--.
Line 55, "numerous of cellular" should read --numerous cellular--.
Lines 56-57, "strategy from" should read --strategy for--.
Line 61, "offers" should read --offer--.

Column 3,
Line 11, "arrows indicates" should read --arrows indicate--.

Column 4,
Line 10, "At pH about" should read --At a pH of about--.
Line 33, "Amount them" should read --Among them--.

Column 5,
Line 37, "than Ina" should read --than IIIa--.
Line 66, "that can" should read --that can be--.

Column 6,
Line 55, "bacteria:" should read --bacteria.--.

Signed and Sealed this
Fourteenth Day of April, 2015

Michelle K. Lee
*Director of the United States Patent and Trademark Office*

Column 7,
Line 26, "of II a" should read --of IIa--.
Line 36, "almost same" should read --almost the same--.